United States Patent
Alimsijah et al.

(10) Patent No.: US 11,857,981 B2
(45) Date of Patent: Jan. 2, 2024

(54) MAGNETIC SEPARATOR FOR AN AUTOMATED SINGLE CELL SEQUENCING SYSTEM

(71) Applicant: 10x Genomics, Inc., Pleasanton, CA (US)

(72) Inventors: Pratomo Alimsijah, Pleasanton, CA (US); John Richard Chevillet, Pleasanton, CA (US)

(73) Assignee: 10x Genomics, Inc., Pleasanton, CA (US)

( * ) Notice: Subject to any disclaimer, the term of this patent is extended or adjusted under 35 U.S.C. 154(b) by 606 days.

(21) Appl. No.: 16/835,090

(22) Filed: Mar. 30, 2020

(65) Prior Publication Data

US 2021/0187515 A1   Jun. 24, 2021

Related U.S. Application Data

(60) Provisional application No. 62/980,768, filed on Feb. 24, 2020, provisional application No. 62/953,050, filed on Dec. 23, 2019.

(51) Int. Cl.
  *B03C 1/28* (2006.01)
  *B01L 3/00* (2006.01)
  *B01L 9/00* (2006.01)
  *B03C 1/01* (2006.01)
  *B03C 1/033* (2006.01)

(52) U.S. Cl.
  CPC .......... *B03C 1/288* (2013.01); *B01L 3/5085* (2013.01); *B01L 3/50855* (2013.01); *B01L 9/523* (2013.01); *B03C 1/01* (2013.01); *B03C 1/0332* (2013.01); *B01L 2400/043* (2013.01); *B03C 2201/18* (2013.01); *B03C 2201/26* (2013.01)

(58) Field of Classification Search
  None
  See application file for complete search history.

(56) References Cited

U.S. PATENT DOCUMENTS

| | | | |
|---|---|---|---|
| 5,658,548 A | 8/1997 | Padhye et al. | |
| 5,705,628 A | 1/1998 | Hawkins | |
| 5,897,783 A * | 4/1999 | Howe | B03C 1/288 |
| | | | 436/526 |
| 6,133,436 A | 10/2000 | Koster et al. | |

(Continued)

FOREIGN PATENT DOCUMENTS

| | | |
|---|---|---|
| EP | 1348966 A2 | 10/2003 |
| EP | 1944368 A1 | 7/2008 |

(Continued)

OTHER PUBLICATIONS

U.S. Appl. No. 17/242,802, Salmanzadeh.

(Continued)

*Primary Examiner* — Krishnan S Menon
(74) *Attorney, Agent, or Firm* — Clark & Elbing LLP

(57) ABSTRACT

A magnetic separator is disclosed. The magnetic separator comprises an array of magnets configured to interact with a tube holder plate, wherein the tube holder plate comprises an array of tubes. The magnetic separator comprises a raised frame extending around a periphery of the array of magnets such that the raised frame is configured to support the tube holder plate such that the array of tubes is suspended above the array of magnets.

16 Claims, 11 Drawing Sheets

(56) References Cited

U.S. PATENT DOCUMENTS

| | | | |
|---|---|---|---|
| 7,718,421 | B2 | 5/2010 | Chen et al. |
| 9,347,056 | B2 | 5/2016 | Saito et al. |
| 9,975,122 | B2 | 5/2018 | Masquelier et al. |
| 10,245,587 | B2 | 4/2019 | Masquelier et al. |
| 10,544,413 | B2 | 1/2020 | Bharadwaj et al. |
| 10,697,000 | B2 | 6/2020 | Belgrader et al. |
| 11,135,584 | B2 | 10/2021 | Masquelier et al. |
| 2002/0174878 | A1* | 11/2002 | Nisson ............... B01L 9/523 134/1 |
| 2003/0027203 | A1 | 2/2003 | Fields |
| 2004/0040851 | A1 | 3/2004 | Karger et al. |
| 2004/0165332 | A1 | 8/2004 | Beson |
| 2004/0214175 | A9 | 10/2004 | McKernan et al. |
| 2004/0228763 | A1 | 11/2004 | Ingenhoven et al. |
| 2005/0013741 | A1 | 1/2005 | a'Brassard |
| 2006/0094108 | A1 | 5/2006 | Yoder et al. |
| 2007/0065808 | A1 | 3/2007 | Bohm et al. |
| 2007/0251341 | A1 | 11/2007 | Balmer |
| 2008/0003142 | A1 | 1/2008 | Link et al. |
| 2009/0305397 | A1 | 12/2009 | Dodgson et al. |
| 2011/0005978 | A1 | 1/2011 | Bohm et al. |
| 2011/0114490 | A1 | 5/2011 | Pamula et al. |
| 2012/0190037 | A1 | 7/2012 | Durin et al. |
| 2012/0196288 | A1 | 8/2012 | Beer |
| 2013/0074944 | A1 | 3/2013 | Van Gelder |
| 2013/0315800 | A1 | 11/2013 | Yin et al. |
| 2014/0235506 | A1 | 8/2014 | Hindson et al. |
| 2015/0031037 | A1 | 1/2015 | Li et al. |
| 2015/0361418 | A1 | 12/2015 | Reed |
| 2016/0298107 | A1 | 10/2016 | O'Farrell et al. |
| 2017/0336306 | A1 | 11/2017 | Miller et al. |
| 2018/0071741 | A1 | 3/2018 | Kelly et al. |
| 2018/0362963 | A1* | 12/2018 | Stelling ............... B03C 1/01 |
| 2019/0039034 | A1* | 2/2019 | Siow ............... B03C 1/0332 |
| 2019/0329245 | A1 | 10/2019 | Masquelier et al. |
| 2020/0115703 | A1 | 4/2020 | Bharadwaj et al. |
| 2020/0391215 | A1 | 12/2020 | Cox et al. |
| 2021/0032678 | A1 | 2/2021 | Belgrader et al. |
| 2021/0293693 | A1 | 9/2021 | Bharadwaj et al. |
| 2022/0097045 | A1 | 3/2022 | Masquelier et al. |
| 2022/0268795 | A1 | 8/2022 | Alimsijah et al. |

FOREIGN PATENT DOCUMENTS

| | | |
|---|---|---|
| EP | 3517974 A1 | 7/2019 |
| EP | 3605109 A1 | 2/2020 |
| WO | WO-03/037515 A1 | 5/2003 |
| WO | WO-2006/071770 A2 | 7/2006 |
| WO | WO-2007/140015 A2 | 12/2007 |
| WO | WO-2010/009365 A1 | 1/2010 |
| WO | WO-2011/059443 A1 | 5/2011 |
| WO | WO-2012/019765 A1 | 2/2012 |
| WO | WO-2012/156744 A2 | 11/2012 |
| WO | WO-2014/182835 A1 | 11/2014 |
| WO | WO-2014/210353 A2 | 12/2014 |
| WO | WO-2015/200717 A2 | 12/2015 |
| WO | WO-2016/137973 A1 | 9/2016 |
| WO | WO-2016/193758 A1 | 12/2016 |
| WO | WO-2018/213643 A1 | 11/2018 |
| WO | WO-2019/169347 A1 | 9/2019 |
| WO | WO-2020/123657 A2 | 6/2020 |

OTHER PUBLICATIONS

U.S. Appl. No. 17/314,756, Salmanzadeh.
U.S. Appl. No. 17/332,371, Salmanzadeh et al.
U.S. Appl. No. 17/338,215, Salmanzadeh et al.
U.S. Appl. No. 17/587,861, Shah.
U.S. Appl. No. 17/851,416, Bharadwaj et al.
Anonymous: "Dynal MPC(TM)-S", Oct. 13, 2008 (Oct. 13, 2008), XP055603532, Retrieved from the Internet on Jul. 9, 2019; URL:<https://www.veritastk.co.jp/products/pdf/120%2020D.Dynal_MPC-S%28rev005%29.pdf>.
Beneyton et al., "High-throughput screening of filamentous fungi using nanoliter-range droplet-based microfluidics," Sci Rep. 6:27223 (Jun. 2016) (10 pages).
Brouzes et al., "Rapid and continuous magnetic separation in droplet microfluidic devices," available in PMC Feb. 7, 2016, published in final edited form as: Lab Chip. 15(3):908-919 (2015) (23 pages).
Chokkalingam et al., "Probing cellular heterogeneity in cytokine-secreting immune cells using droplet-based microfluidics," Lab Chip. 13(24): 4740-4744 (2013).
Hu et al., "Efficient cell pairing in droplets using dual-color sorting," Lab Chip. 15(20):3989-93 (2015).
International Search Report and Written Opinion for PCT Application No. PCT/US2020/061116, dated Apr. 12, 2021 (18 pages).
Jo et al., "Magnetophoretic sorting of single cell-containing microdroplets," Micromachines (Basel). 7(4): 56 (2016) (9 pages).
Klein et al., "Droplet barcoding for single-cell transcriptomics applied to embryonic stem cells," Cell. 161(5): 1187-1201 (2015) (May 21, 2015) (22 pages).
Lagus et al., "A review of the theory, methods and recent applications of high-throughput single-cell droplet microfluidics," Journal of Physics D: Applied Physics. 46:114005 (2013) (21 pages).
Lennon et al., "A scalable, fully automated process for construction of sequence-ready barcoded libraries for 454," Genome Biol. 11(2):R15 (2010) (9 pages).
Shembekar et al., "Droplet-based microfluidics in drug discovery, transcriptomics and high-throughput molecular genetics," Lab Chip. 16(8):1314-31 (Mar. 2016).

* cited by examiner

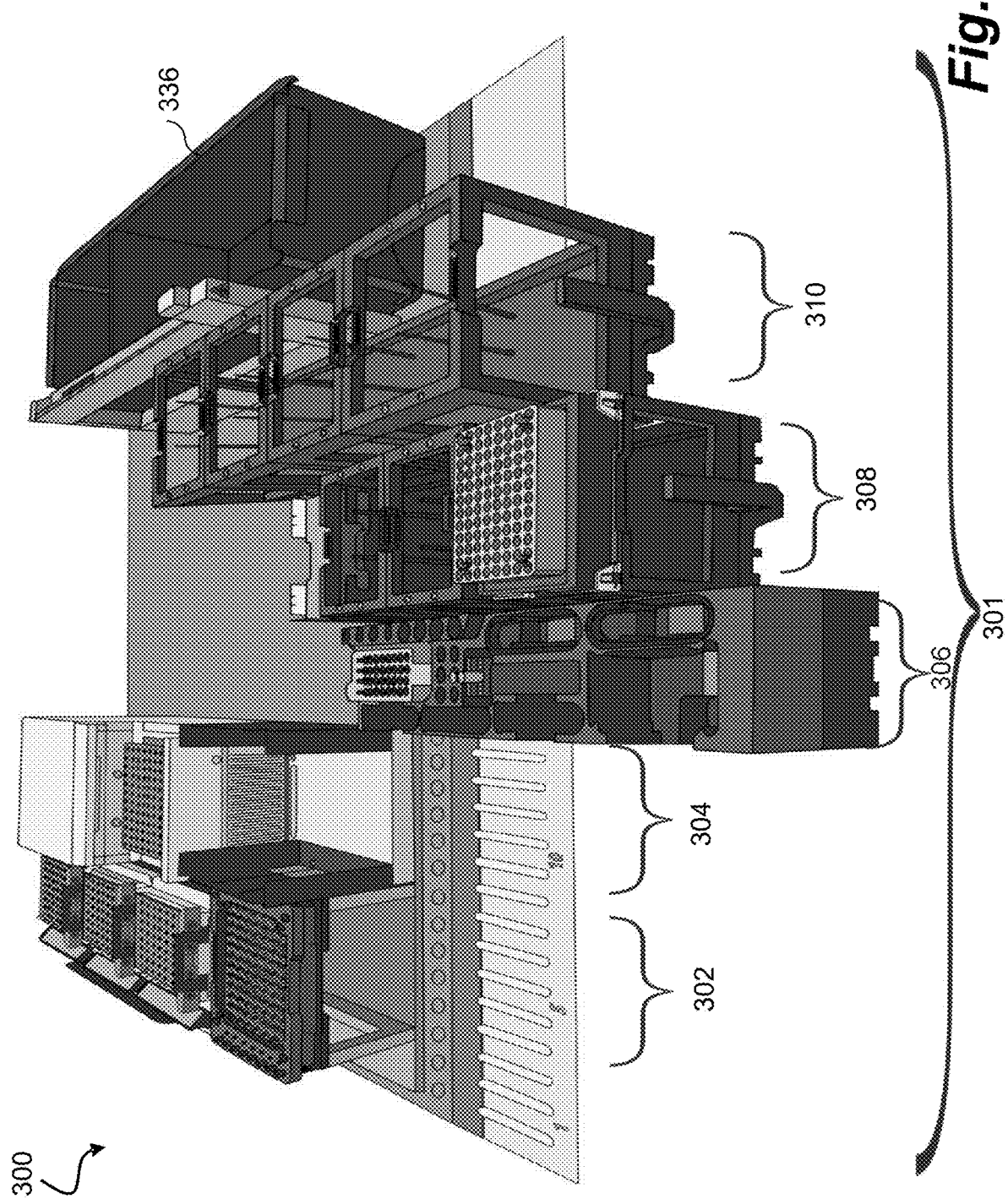

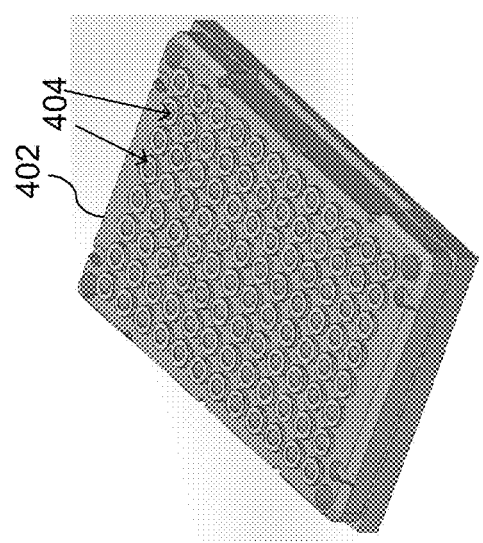
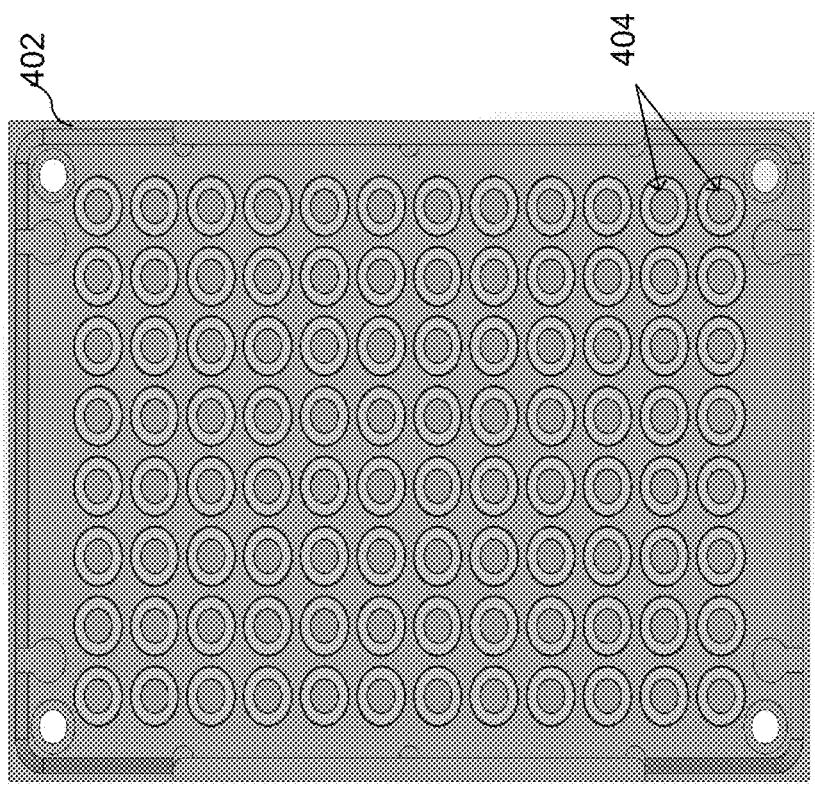
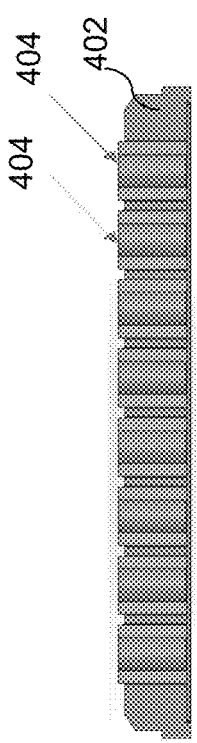

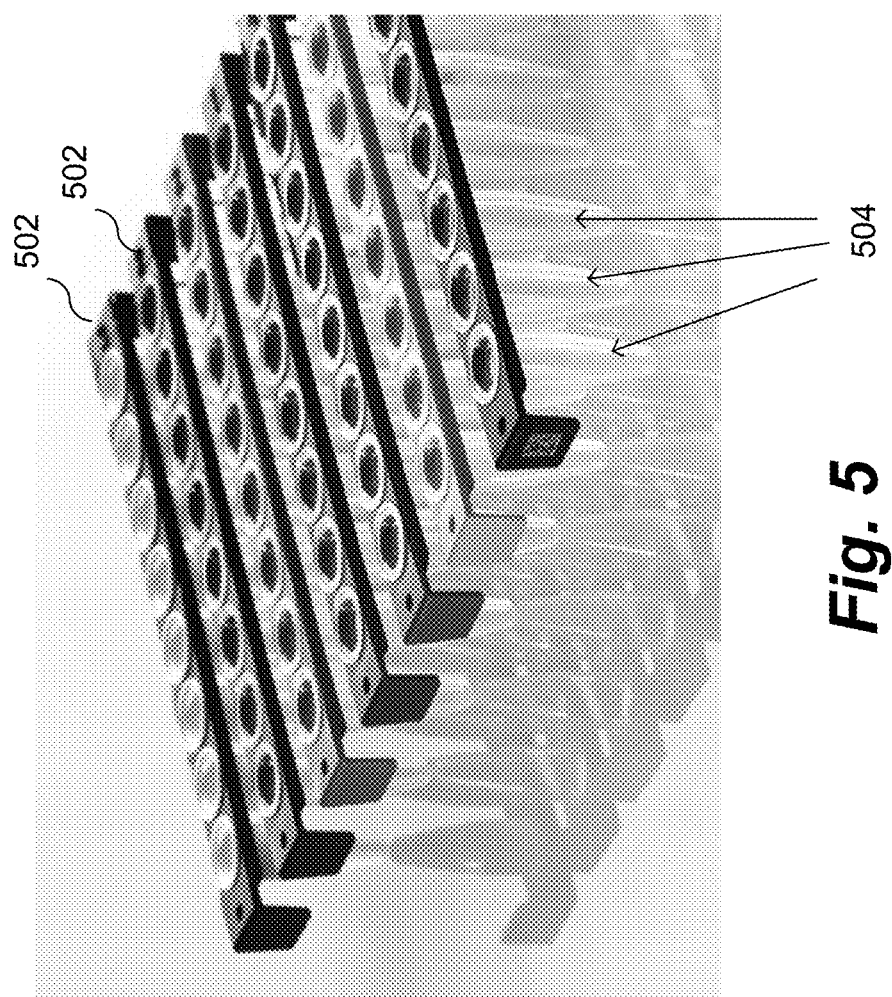

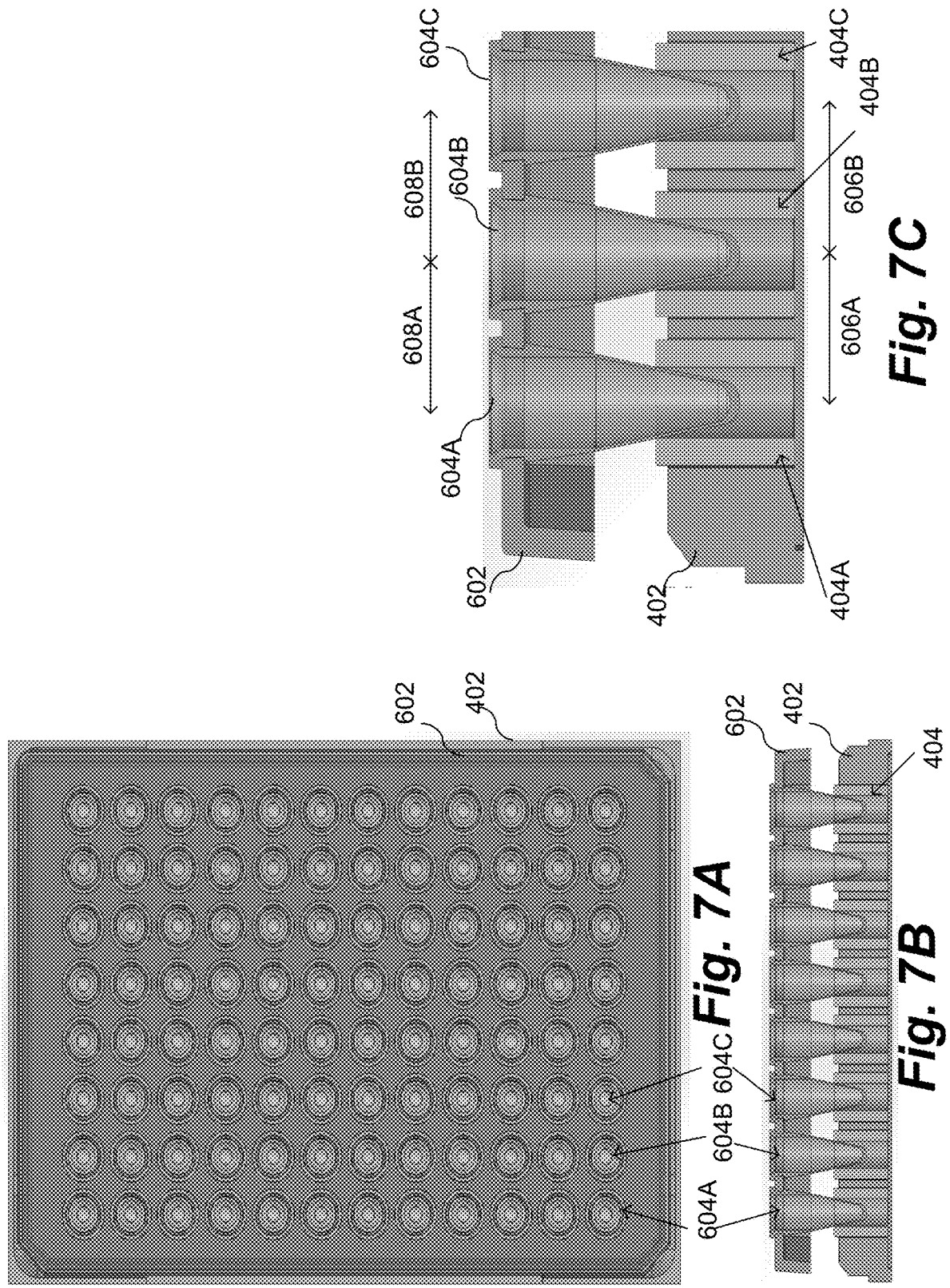

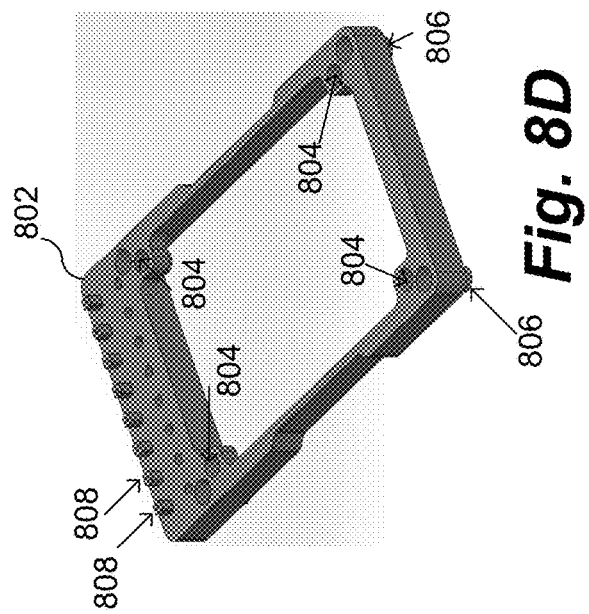
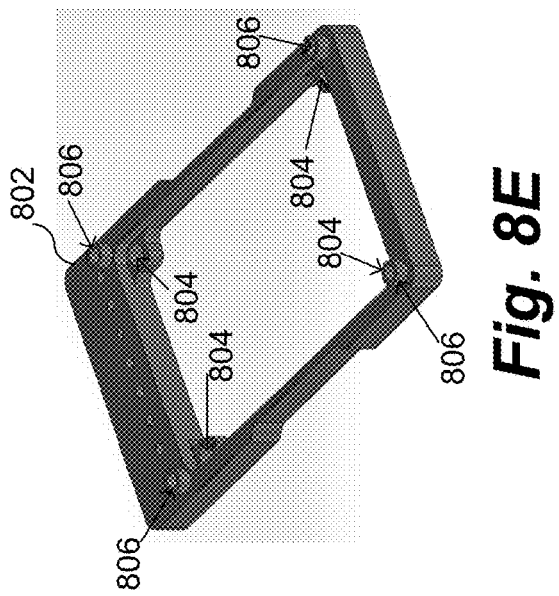
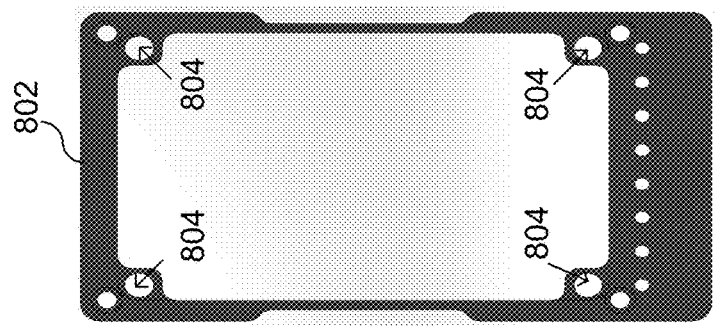
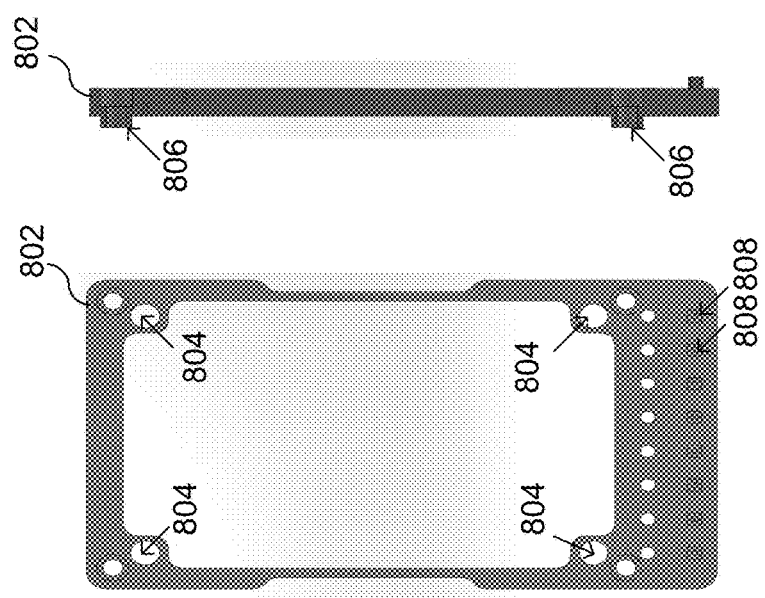

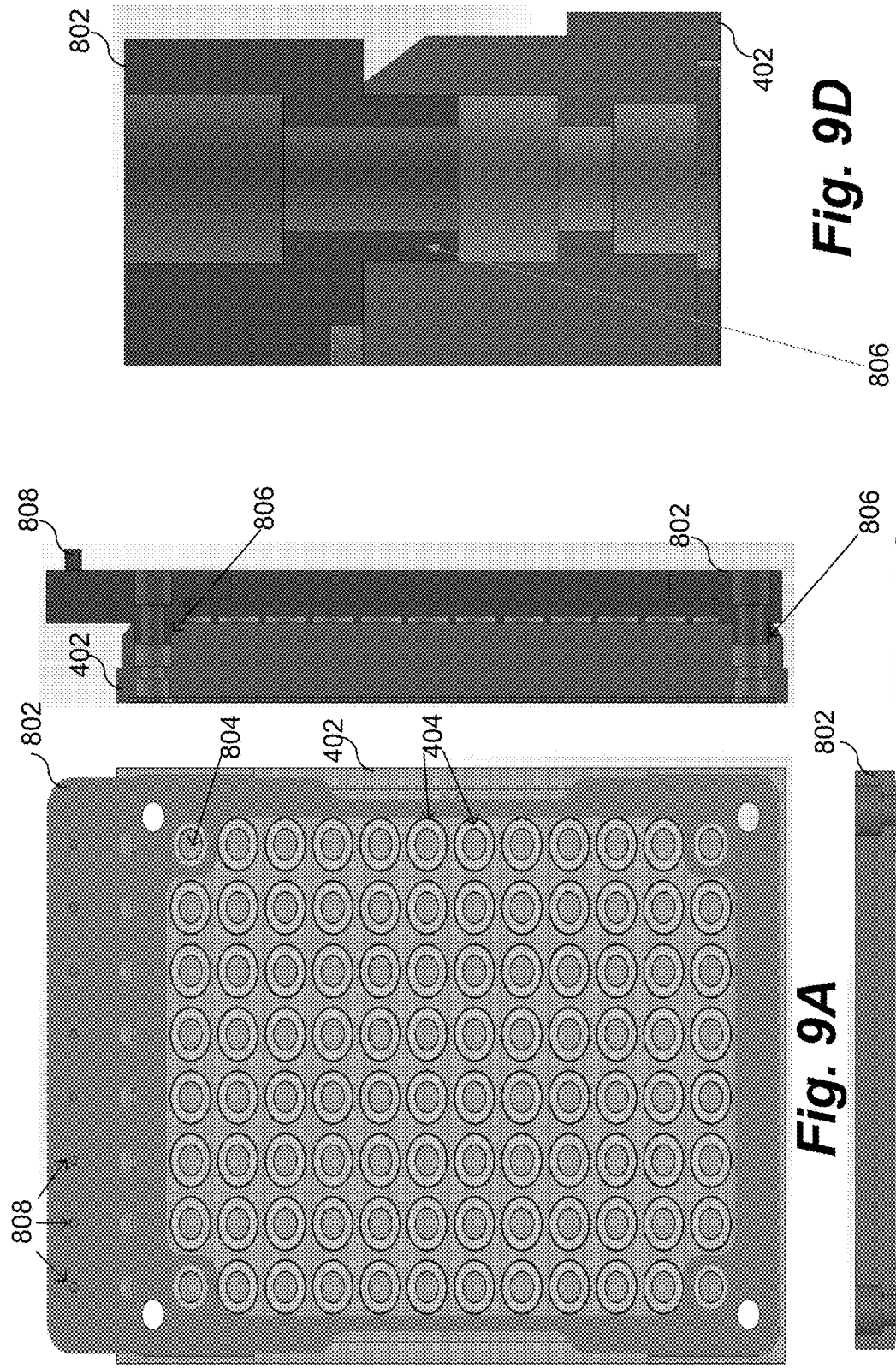

MAGNETIC SEPARATOR FOR AN AUTOMATED SINGLE CELL SEQUENCING SYSTEM

CROSS REFERENCE TO OTHER APPLICATIONS

This application claims priority to U.S. Provisional Patent Application No. 62/953,050 entitled AUTOMATED SINGLE CELL SEQUENCING SYSTEM filed Dec. 23, 2019 and U.S. Provisional Patent Application No. 62/980,768 entitled MAGNETIC SEPARATOR FOR AN AUTOMATED SINGLE CELL SEQUENCING SYSTEM filed Feb. 24, 2020, both of which are incorporated herein by reference for all purposes.

BACKGROUND OF THE INVENTION

Ribonucleic acid (RNA) is a polymeric molecule essential in various biological roles in coding, decoding, regulation and expression of genes. RNA-sequencing (RNA-Seq) uses next-generation sequencing (NGS) to reveal the presence and quantity of RNA in a biological sample at a given moment. RNA-Seq analyzes the transcriptome of gene expression patterns encoded within the RNA.

Traditional RNA-Seq techniques analyze the RNA of an entire population of cells, but only yield a bulk average of the measurement instead of representing each individual cell's transcriptome. By analyzing the transcriptome of a single cell at a time, the heterogeneity of a sample is captured and resolved to the fundamental unit of living organisms—the cell. Single-cell transcriptomics examines the gene expression level of individual cells in a given population by simultaneously measuring the messenger RNA (mRNA) concentration of hundreds to thousands of genes.

Automated single cell sequencing systems have been developed integrating various components to achieve RNA sequencing. One important component is a magnetic separator which interacts with a fluid in a vial. There is a need to improve the interaction in a way that allows fluid to be used efficiently and to provide consistent results.

BRIEF DESCRIPTION OF THE DRAWINGS

Various embodiments of the invention are disclosed in the following detailed description and the accompanying drawings.

FIG. 3 illustrates yet another view of one embodiment of an automated single cell sequencing system 300.

FIG. 4A illustrates a top view of an embodiment of a magnetic separator plate 402.

FIG. 4B illustrates a cross sectional view of the magnetic separator plate 402.

FIG. 4C illustrates another view of the magnetic separator plate 402.

FIG. 5 illustrates a plurality of strip tubes 502 that may be loaded onto the magnetic separator plate 214 where the magnetic bead based cleanup may be performed.

FIG. 7A illustrates a top view of the 96-tube PCR plate 602 being loaded onto the magnetic separator plate 402.

FIG. 7B illustrates a cross sectional view of the 96-tube PCR plate 602 being loaded onto the magnetic separator plate 402.

FIG. 7C illustrates a portion of a magnified cross sectional view of the 96-tube PCR plate 602 being loaded onto the magnetic separator plate 402.

FIG. 8A illustrates a top view of a magnetic separator plate adapter 802.

FIG. 8B illustrates a cross sectional view of the magnetic separator plate adapter 802.

FIG. 8C illustrates a bottom view of the magnetic separator plate adapter 802.

FIG. 8D illustrates another view of the top surface of the magnetic separator plate adapter 802.

FIG. 8E illustrates another view of the bottom surface of the magnetic separator plate adapter 802.

FIG. 9A illustrates a top view of the magnetic separator plate adapter 802 being loaded onto the magnetic separator plate 402.

FIG. 9B illustrates a cross sectional view of the magnetic separator plate adapter 802 being loaded onto the magnetic separator plate 402.

FIG. 9C illustrates another cross sectional view of the magnetic separator plate adapter 802 being loaded onto the magnetic separator plate 402.

FIG. 9D illustrates a portion of a magnified cross sectional view of the magnetic separator plate adapter 802 being loaded onto the magnetic separator plate 402.

DETAILED DESCRIPTION

Figure 1:
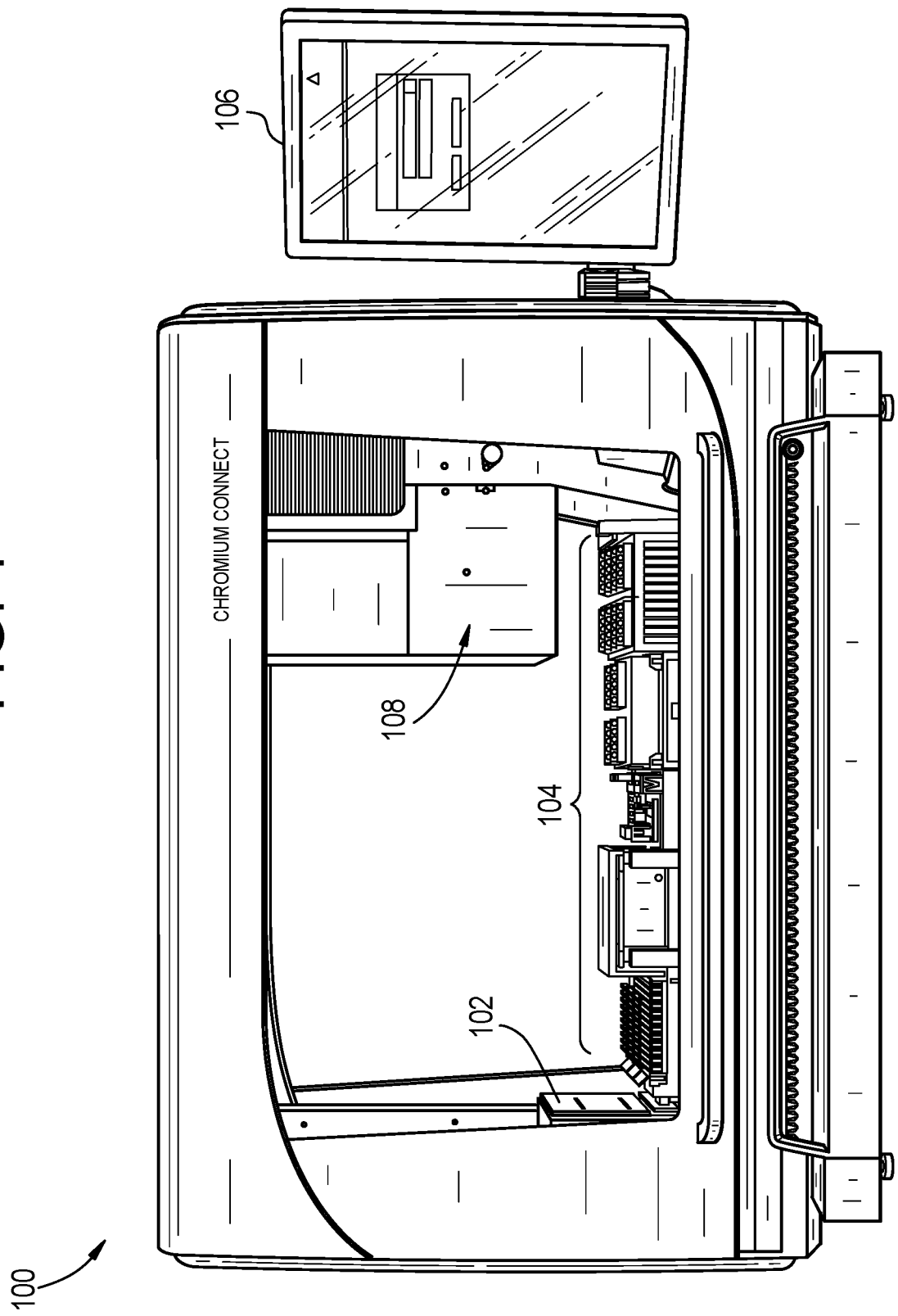
FIG. 1 illustrates a front view of one embodiment of an automated single cell sequencing system 100.

The invention can be implemented in numerous ways, including as a process; an apparatus; a system; a composition of matter; a computer program product embodied on a computer readable storage medium; and/or a processor, such as a processor configured to execute instructions stored on and/or provided by a memory coupled to the processor. In this specification, these implementations, or any other form that the invention may take, may be referred to as techniques. In general, the order of the steps of disclosed processes may be altered within the scope of the invention. Unless stated otherwise, a component such as a processor or a memory described as being configured to perform a task may be implemented as a general component that is temporarily configured to perform the task at a given time or a specific component that is manufactured to perform the task. As used herein, the term 'processor' refers to one or more devices, circuits, and/or processing cores configured to process data, such as computer program instructions.

A detailed description of one or more embodiments of the invention is provided below along with accompanying figures that illustrate the principles of the invention. The invention is described in connection with such embodiments, but the invention is not limited to any embodiment. The scope of the invention is limited only by the claims and the invention encompasses numerous alternatives, modifications and equivalents. Numerous specific details are set forth in the following description in order to provide a thorough understanding of the invention. These details are provided for the purpose of example and the invention may be practiced according to the claims without some or all of these specific details. For the purpose of clarity, technical material that is known in the technical fields related to the invention has not been described in detail so that the invention is not unnecessarily obscured.

Preparing consistent single cell gene expression libraries is labor intensive and requires extensive hands-on (i.e., manual) time. It would be beneficial if this could be automated, freeing lab personnel to perform other tasks.

Automated techniques for the preparation of single cell gene expression libraries are disclosed in the present application. The techniques provided herein allow for the maximization of consistency in the libraries prepared and productivity of the personnel. The techniques improve quality and performance by 1) decreasing technical variability and generating reproducible results; 2) running pre-validated protocols for single cell assays; and 3) providing a robust workflow and ready-to-use solution. The techniques save time and resources by 1) reducing hands-on time in the lab; 2) eliminating the need for dedicated resources; and 3) requiring no specialized expertise. The techniques are integrated and validated. Single cell partitioning, barcoding, and library preparation are integrated together in one optimized instrument. As a result, less customization and optimization are needed, thereby improving productivity.

FIG. 1 illustrates a front view of one embodiment of an automated single cell sequencing system 100. The system includes an automated controller 102 on deck for single cell partitioning and barcoding. Reagents and consumables may be loaded onto the deck area 104 at the beginning of each run. Operations may be guided through an easy-to-use touchscreen computer 106 with Internet connectivity. System 100 includes a liquid handling gantry 108 that may perform pipetting steps throughout the entire single cell workflow. System 100 further includes one or more barcode scanners that enable lot and reagent tracking for reagents and consumables.

Figure 2:
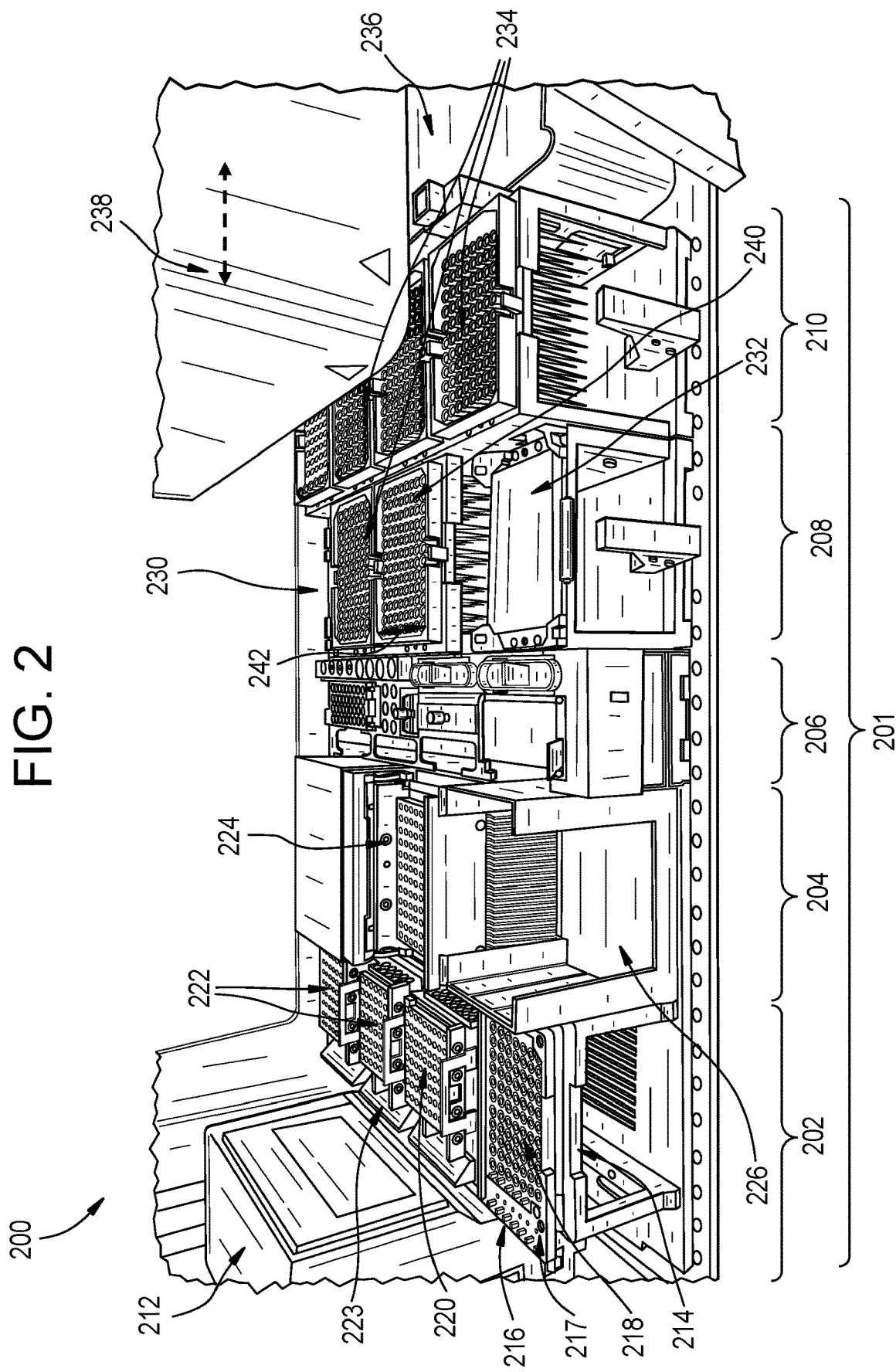
FIG. 2 illustrates another view of one embodiment of an automated single cell sequencing system 200.

FIG. 2 illustrates another view of one embodiment of an automated single cell sequencing system 200. Automated single cell sequencing system 200 includes five carriers (202, 204, 206, 208, and 210) on the deck 201. Some of the carriers are stationary and some of the carriers may slide in and out for loading and unloading items. Each of the carriers may be loaded with different types of labwares, modules, and consumables, such as a magnetic separator plate, a thermal cycler block, tips, reagent reservoirs, plates (e.g., polymerase chain reaction (PCR) plates and deep well plates), tubes, and the like. The terms labwares and modules may be used interchangeably in the present application.

FIG. 3 illustrates yet another view of one embodiment of an automated single cell sequencing system 300. Automated single cell sequencing system 300 includes five carriers (302, 304, 306, 308, and 310) and a disposal bin 336 on a deck 301.

As shown in FIG. 2, an automated controller 212 for single cell partitioning and barcoding is located adjacent to the left most carrier 202. The leftmost carrier 202 includes a magnetic separator plate 214. An array of magnets 218 is located above magnetic separator plate 214. Arrays of wells, tips or tubes may be placed above the array of magnets 218. In some embodiments, a magnetic separator plate adapter 217 may be mounted on top of the magnetic separator plate 214 to keep the array of tips/tubes stable and sitting at the exact locations. The magnetic separator plate adapter 217 may rest above the magnetic separator plate 214 and the array of magnets 218. The magnetic separator plate adapter 217 may be formed of plastic and include skirts. Magnetic separator plate adapter 217 may include a plurality of calibration posts 216. Carrier 202 may further receive a cold plate reagent module 220 and other reagent modules 222.

In some embodiments, automated single cell sequencing system 200 may include a barcode reading system. A barcode reader is used to scan reagents and consumables. The barcode reading system enables experiment tracking and prevents reagent mix-ups. A barcode reader (not shown in FIG. 2) may be placed above the five carriers (202, 204, 206, 208, and 210) on deck 201. The barcode reader may be used to read the slots for holding the tips/tubes and the tips/tubes that go into the slots at different locations. The barcode reading system may include software logic to make sure that the right tubes (with reagents) are put at the right slots. The barcode reading system may also detect that the tubes are missing such that the system may inform the user about these errors. The system may check for color matching, lot numbers, and expiration dates. As shown in FIG. 2, automated single cell sequencing system 200 may include a plurality of mirrors 223 to allow the barcode reader to read sideways and at more locations. In some embodiments, stickers with barcodes on the slots are covered by the tips/tubes if they are placed there. If the barcode reader reads the barcodes on the slots, then the slots are determined as being empty. If the barcode reader reads the barcodes on the tips/tubes, then the system may match the two barcodes.

Carrier 204 (the second carrier from the left) includes an on-deck thermal cycler 224 (ODTC). A thermal cycler may be used to amplify segments of Deoxyribonucleic acid (DNA) via the polymerase chain reaction (PCR). Thermal cyclers may also be used to facilitate other temperature-sensitive reactions. In some embodiments, a thermal cycler has a thermal block with holes where tubes holding reaction mixtures may be inserted. The thermal cycler then raises and lowers the temperature of the block in discrete, pre-programmed steps. Carrier 204 further includes a rack 226 for storing disposable ODTC lids.

Carrier 206 (the third carrier from the left) includes carrier spaces for receiving, storing, or loading tube strips, chips, gel beads, core or lifting paddles, ethanol reservoirs, primer, glycerol, and the like. Carrier 208 (the fourth carrier from the left) includes a sample index plate holder 230. The carrier further includes a unit 232 for formulations and bead cleanups. Carrier 208 and carrier 210 (the fifth carrier from the left) may receive different consumables, such as pipette tips 234.

Automated single cell sequencing system 200 may further include a waste disposal bin 236 that is adjacent to carrier 210. In some embodiments, a divider may be added to the waste disposal bin for separating the recycled tips and lids. With the added divider, one side of the disposal bin is used for storing the tips and the other side of the disposal bin is used for storing the lids. A gantry 238 may be programmed to drop the tips and the lids on different sides of the disposal bin. This prevents the lids from stacking up and toppling over, causing the system to malfunction. This allows the recycling of the lids while preventing contamination.

The liquid handling gantry 238 in automated single cell sequencing system 200 may perform automated pipetting steps throughout the entire single cell workflow. Liquid handling gantry 238 is a movable liquid-handling pipetting device with precision positioning.

A traditional manual pipette is a laboratory tool commonly used in chemistry, biology and medicine to transport a measured volume of liquid. A pipette can be used to aspire (or draw up) a liquid into a pipette tip and dispense the liquid. In manual pipetting, a piston is moved by a thumb using an operation knob. Accuracy and precision of pipetting depend on the expertise of the human operator.

Automated pipetting has many advantages over manual pipetting. Automated pipetting enhances the throughput and the reproducibility of laboratory experiments. Automated pipetting takes the manual labor out of repeated pipetting, thereby shortening manual hands-on time. Reducing manual hands-on time frees up time and effort for other tasks, thereby greatly improving throughput. Furthermore, automated pipetting significantly reduces errors from manual pipetting, thereby enhancing reproducibility.

The liquid handling gantry 238 in automated single cell sequencing system 200 includes a pipetting head, which is the mechanical component for liquid transfer. In some embodiments, the pipetting head is a multi-channel pipetting head for increased throughput. In some embodiments, the pipetting head may be an 8-channel pipetting head coupled to a pump system such that for each channel, a volume of liquid may be aspirated from a source container by creating suction and then dispensed into a destination container (e.g., a tube or a well). A disposable tip may be attached to each of the eight channels of the pipetting head, such that the liquid is not in direct contact with the pipetting head, preventing cross contamination.

The liquid handling gantry 238 with the pipetting head may be programmed to move within a working area where liquid aspirating and dispensing take place. The working area may be the deck area 201 including the five carriers (202, 204, 206, 208, and 210) that may be loaded with different types of labwares, modules, or consumables, such as reagent reservoirs, plates (e.g., polymerase chain reaction (PCR) plates and deep well plates), tubes, and the like. For example, the pipetting head may be moved to the position of the reagent module 240 to dispense liquid into a row 242 of eight wells of the reagent module 240. The position of the reagent module 240 and the position of the row of wells may each be specified by a set of offset distances in the x, y, and z axes from one or more reference points within deck area 201. In some embodiments, the position of a certain module or labware may be recorded by single cell sequencing system 200 as a first set of offset values (in x, y, and z) from a reference point within deck area 201, and the position of a row of wells within the module or labware may further be recorded by the system as another set of offset values from the position of the module or labware. In some embodiments, different positions within the working area are recorded by single cell sequencing system 200 as different sets of offset values from a single reference point within deck area 201.

In order to place the pipetting head into the appropriate source and destination containers, the liquid handling gantry 238 with the pipetting head may be moved by one or more actuators to different x and y positions in a plane substantially parallel to the floor of deck 201. In addition, the pipetting head may be moved by one or more actuators in a direction substantially perpendicular to the plane, such that the pipetting head and the tips attached to the pipetting head may be inserted into or withdrawn from the source and destination containers.

Magnetic separator plate 214 in FIG. 2 performs magnetic bead based cleanup. Magnetic beads are used for DNA purification and fragment size selection. Automated single cell sequencing system 200 uses the single-cell RNA-seq technology to analyze transcriptomes on a cell-by-cell basis through the use of microfluidic partitioning to capture single cells and prepare barcoded, next-generation sequencing (NGS) cDNA libraries. Specifically, single cells, reverse transcription (RT) reagents, gel beads containing barcoded oligonucleotides, and oil are combined on a microfluidic chip to form reaction vesicles called Gel Beads in Emulsion, or GEMs. After incubation, GEMs are broken and pooled fractions are recovered. Silane magnetic beads are used to purify the first-strand cDNA from the post GEM-RT reaction mixture, which includes leftover biochemical reagents and primers. In particular, consumables (e.g., test tubes or wells) containing the post GEM-RT reaction mixture and the magnetic beads may be loaded onto the magnetic separator plate 214 where the magnetic bead based cleanup is performed. Barcoded, full-length cDNA is then amplified via PCR to generate sufficient mass for library construction.

FIG. 4A illustrates a top view of an embodiment of a magnetic separator plate 402. FIG. 4B illustrates a cross sectional view of the magnetic separator plate 402. FIG. 4C illustrates another view of the magnetic separator plate 402.

As shown in FIG. 4A, magnetic separator plate 402 is a magnet holder plate that holds an array of magnets 404. Magnetic separator plate 402 is a 96-ring magnet plate, and the array of magnets 404 is an 8×12 array of magnets with eight magnets in a row and twelve magnets in a column. In some embodiments, each of the magnets 404 is a ring magnet. As shown in FIG. 4B, a ring magnet may be a magnet with a shape of a hollow cylinder that is empty from inside and with differing internal and external radii. The hollow space of the cylinder allows a bottom end of a tube to be inserted therein. For example, a tube received by a ring magnet may be a finger-like length of glass or plastic tubing that is open at the top and closed at the bottom.

FIG. 5 illustrates a plurality of strip tubes 502 that may be loaded onto the magnetic separator plate 214 or magnetic separator plate 402 where the magnetic bead based cleanup may be performed. As shown in FIG. 5, each of the strip tubes 502 includes eight tubes 504 for storing the reaction mixture and the magnetic beads.

Figure 6:
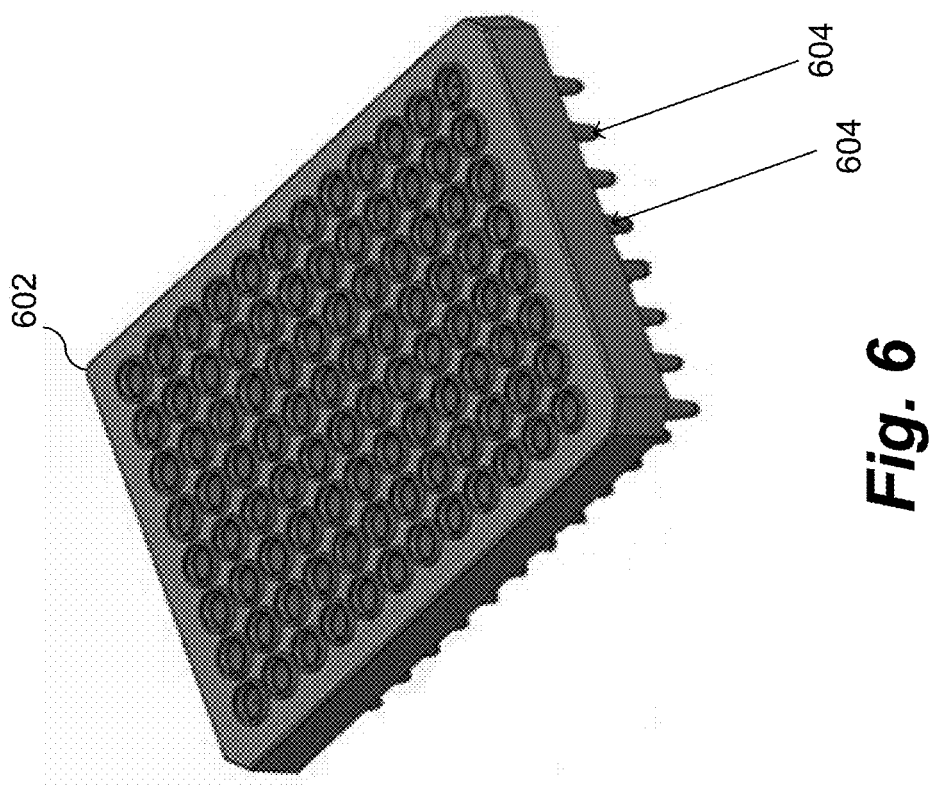
FIG. 6 illustrates an exemplary consumable 602 that may be loaded onto the magnetic separator plate 214 where the magnetic bead based cleanup may be performed.

FIG. 6 illustrates an exemplary consumable 602 that may be loaded onto the magnetic separator plate 214 or magnetic separator plate 402 where the magnetic bead based cleanup may be performed. In this example, consumable 602 is a 96-tube polymerase chain reaction (PCR) tube holder plate with an array of tubes 604 arranged as an 8×12 array of tubes with eight tubes in a row and twelve tubes in a column.

FIG. 7A illustrates a top view of the 96-tube PCR plate 602 being loaded onto the magnetic separator plate 402. FIG. 7B illustrates a cross sectional view of the 96-tube PCR plate 602 being loaded onto the magnetic separator plate 402. FIG. 4C illustrates a portion of a magnified cross-sectional view of the 96-tube PCR plate 602 being loaded onto the magnetic separator plate 402.

As shown in FIGS. 7B and 7C, the hollow space of a ring magnet (e.g., 404A or 404B) allows the bottom end of a tube (e.g., 604A or 604B) to be inserted therein. However, both the PCR plate 602 and the magnetic separator plate 402 are manufactured parts that have their respective sets of associated tolerances. All dimensions of a manufactured part have their associated tolerance, the amount that the particular dimension is allowed to vary. The tolerance is the difference between the maximum and minimum limits. Therefore, the length 606A (the length from the center of the ring magnet 404A to the center of the ring magnet 404B) and the length 606B (the length from the center of the ring magnet 404B to the center of the ring magnet 404C) may not be the same. Similarly, the length 608A (the length from the center of the tube 604A to the center of the tube 604B) and the length 608B (the length from the center of the tube 608B to the center of the tube 604C) may not be the same. These variations in dimensions may cause misalignments of the tubes and their corresponding ring magnets. As a result, some of the bottom ends of the tubes may no longer be inserted into the hollow spaces and resting within the hollow spaces of the ring magnets at the same depth, causing the PCR plate 602 to be tilted instead of leveled, and causing it to rest on the magnetic separator plate 402 at an angle, thereby degrading the performance of the magnetic bead based cleanup process.

In the present application, an improved magnetic separator is disclosed. The magnetic separator comprises an array of magnets configured to interact with an array of tubes, wherein the array of tubes is attached to a plate. The magnetic separator further includes a magnetic separator plate adapter. In some embodiments, the adapter comprises a raised frame extending around a periphery of the array of magnets such that the raised frame is configured to support the plate, such that the array of tubes are suspended above the array of magnets. By suspending the array of tubes above the array of magnets, the bottom ends of the tubes are no longer resting within the hollow spaces of the ring magnets at different depths, thereby keeping the plate with the array of tubes leveled with respect to the array of magnets. The benefit is that the performance of the magnetic bead based cleanup process may be significantly improved.

FIG. 8A illustrates a top view of a magnetic separator plate adapter 802. FIG. 8B illustrates a cross sectional view of the magnetic separator plate adapter 802. FIG. 8C illustrates a bottom view of the magnetic separator plate adapter 802. FIG. 8D illustrates another view of the top surface of the magnetic separator plate adapter 802. FIG. 8E illustrates another view of the bottom surface of the magnetic separator plate adapter 802. As shown in FIG. 8A, magnetic separator plate adapter 802 includes four collars 804 at the four corners of the adapter. The collars 804 may be used to fix the location (the x and y location on the deck) of a consumable, such as a 96-tube PCR plate. For example, each of the collars 804 constrains the x location and the y location of the tube holder plate by having a tube inserted into the collar. The magnetic separator plate adapter 802 further includes four cylindrical feet 806 at the four corners of the adapter, such that the magnetic separator plate adapter 802 may be mounted on the magnetic separator plate 402. In some embodiments, magnetic separator plate adapter 802 may be formed of plastic and includes skirts. Magnetic separator plate adapter 802 may include a plurality of calibration posts 808.

FIG. 9A illustrates a top view of the magnetic separator plate adapter 802 being loaded onto the magnetic separator plate 402. FIG. 9B illustrates a cross sectional view of the magnetic separator plate adapter 802 being loaded onto the magnetic separator plate 402. FIG. 9C illustrates another cross sectional view of the magnetic separator plate adapter 802 being loaded onto the magnetic separator plate 402. FIG. 9D illustrates a portion of a magnified cross sectional view of the magnetic separator plate adapter 802 being loaded onto the magnetic separator plate 402. As shown in FIGS. 9B, 9C, and 9D, a cylindrical foot 806 of the magnetic separator plate adapter 802 fits into a cylindrical hole on the magnetic separator plate 402, thereby mounting the magnetic separator plate adapter 802 on the magnetic separator plate 402 and raising the magnetic separator plate adapter 802 above the magnetic separator plate 402.

Figure 10B:
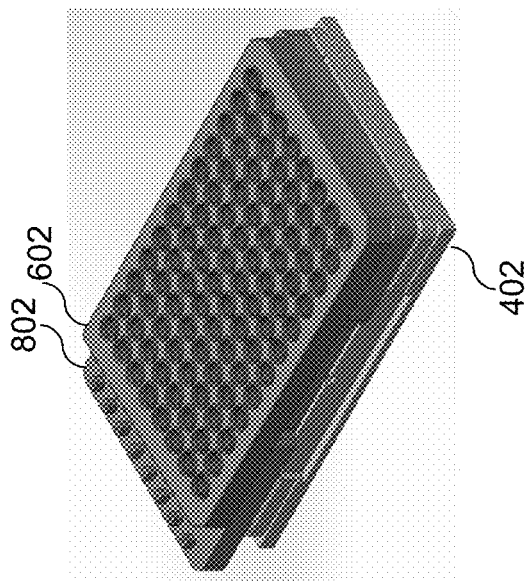
FIG. 10B illustrates another view of the magnetic separator plate adapter 802 being loaded onto the magnetic separator plate 402 and the 96-tube PCR plate 602 being loaded onto the magnetic separator plate adapter 802.
Figure 10A:
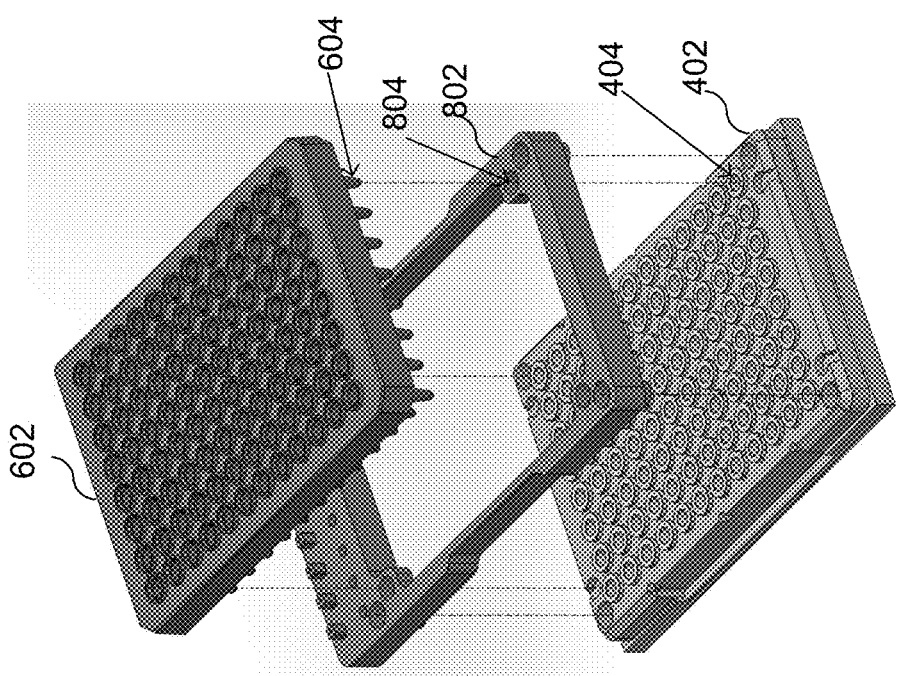
FIG. 10A illustrates a view of the magnetic separator plate adapter 802 about to be loaded onto the magnetic separator plate 402 and the 96-tube PCR plate 602 about to be loaded onto the magnetic separator plate adapter 802.

FIG. 10A illustrates a view of the magnetic separator plate adapter 802 about to be loaded onto the magnetic separator plate 402 and the 96-tube PCR plate 602 about to be loaded onto the magnetic separator plate adapter 802. FIG. 10B illustrates another view of the magnetic separator plate adapter 802 being loaded onto the magnetic separator plate 402 and the 96-tube PCR plate 602 being loaded onto the magnetic separator plate adapter 802.

Figures 11A, 11B, 11C, 11D:
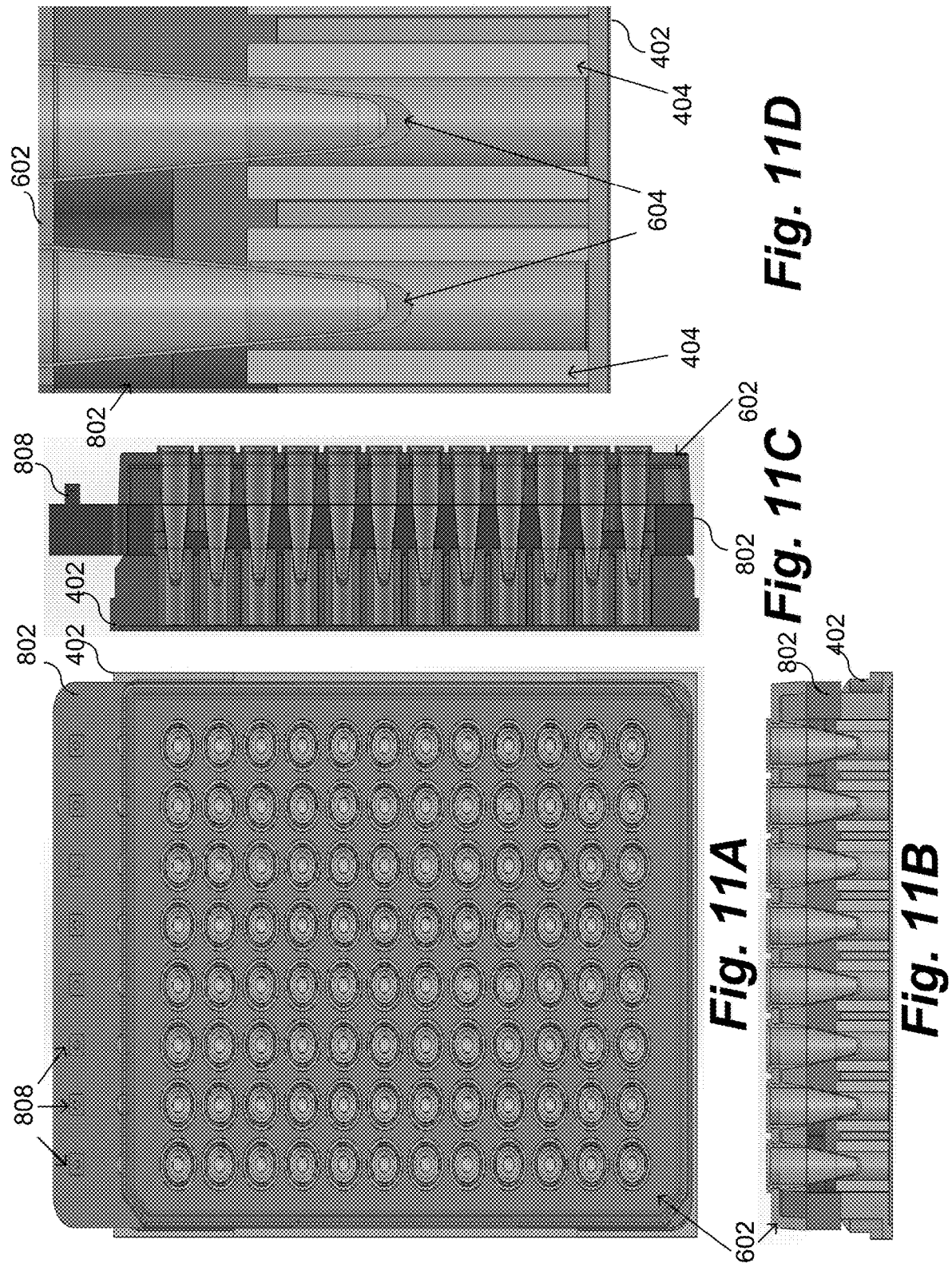
FIG. 11A illustrates a top view of the magnetic separator plate adapter 802 being loaded onto the magnetic separator plate 402, and the 96-tube PCR plate 602 being loaded onto the magnetic separator plate adapter 802.
FIG. 11B illustrates a cross sectional view of the magnetic separator plate adapter 802 being loaded onto the magnetic separator plate 402, and the 96-tube PCR plate 602 being loaded onto the magnetic separator plate adapter 802.
FIG. 11C illustrates another cross-sectional view of the magnetic separator plate adapter 802 being loaded onto the magnetic separator plate 402, and the 96-tube PCR plate 602 being loaded onto the magnetic separator plate adapter 802.
FIG. 11D illustrates a portion of a magnified cross sectional view of the magnetic separator plate adapter 802 being loaded onto the magnetic separator plate 402, and the 96-tube PCR plate 602 being loaded onto the magnetic separator plate adapter 802.

FIG. 11A illustrates a top view of the magnetic separator plate adapter 802 being loaded onto the magnetic separator plate 402, and the 96-tube PCR plate 602 being loaded onto the magnetic separator plate adapter 802. FIG. 11B illustrates a cross-sectional view of the magnetic separator plate adapter 802 being loaded onto the magnetic separator plate 402, and the 96-tube PCR plate 602 being loaded onto the magnetic separator plate adapter 802. FIG. 11C illustrates another cross-sectional view of the magnetic separator plate adapter 802 being loaded onto the magnetic separator plate 402, and the 96-tube PCR plate 602 being loaded onto the magnetic separator plate adapter 802. FIG. 11D illustrates a portion of a magnified cross-sectional view of the magnetic separator plate adapter 802 being loaded onto the magnetic separator plate 402, and the 96-tube PCR plate 602 being loaded onto the magnetic separator plate adapter 802

The magnetic separator plate adapter 802 comprises a raised frame extending around the periphery of the magnetic separator plate 402, such that the raised frame supports the 96-tube PCR plate 602 in such a way that the array of tubes 604 are suspended above the array of magnets 404. As shown in FIG. 11D, the array of tubes is suspended above the array of magnets 404 at a height such that the tubes 604 do not come in contact with their corresponding magnets 404. By suspending the array of tubes 604 above the array of magnets 404, the bottom ends of the tubes 604 are no longer resting within the hollow spaces of the ring magnets at different depths, thereby keeping the 96-tube PCR plate 602 with the array of tubes 604 leveled with respect to the array of magnets 404. The benefit is that the performance of the magnetic bead based cleanup process may be significantly improved.

Although the foregoing embodiments have been described in some detail for purposes of clarity of understanding, the invention is not limited to the details provided. There are many alternative ways of implementing the invention. The disclosed embodiments are illustrative and not restrictive.

What is claimed is:

1. A magnetic separator, comprising:
an array of magnets configured to interact with a tube holder plate, wherein the tube holder plate comprises an array of tubes, wherein the array of magnets and the array of tubes are two-dimensional and each tube of the array of tubes has a different corresponding magnet of the array of magnets; and
a raised frame extending around a periphery of the array of magnets such that the raised frame is configured to support the tube holder plate such that the array of tubes is suspended above the array of magnets.

2. The magnetic separator of claim 1, wherein the array of tubes is suspended above the array of magnets at a height such that each tube of the array of tubes does not come in contact with the corresponding magnet of the array of magnets.

3. The magnetic separator of claim 1, wherein the array of magnets comprises an array of ring magnets, and wherein the array of tubes is suspended above the array of ring magnets such that the bottom ends of the tubes are not resting within the hollow spaces of the ring magnets at different depths.

4. The magnetic separator of claim 3, wherein the array of tubes is suspended above the array of ring magnets such that the tube holder plate is leveled with respect to the array of ring magnets.

5. The magnetic separator of claim 1, wherein the array of magnets is held by a magnet holder plate, and wherein the raised frame comprises a plurality of feet, wherein each foot of the plurality of feet fits into a corresponding hole on the magnet holder plate such that the raised frame is mounted on the magnet holder plate.

6. The magnetic separator of claim 5, wherein the raised frame is mounted on the magnet holder plate such that the raised frame is raised above the magnet holder plate.

7. The magnetic separator of claim 1, wherein the raised frame comprises a plurality of collars, wherein each of the collars constrains a x location and a y location of the tube holder plate.

8. The magnetic separator of claim 7, wherein each of the collars constrains the x location and the y location of the tube holder plate by having a tube of the array of tubes inserted into the collar.

9. A method, comprising:
providing an array of magnets configured to interact with a tube holder plate, wherein the tube holder plate comprises an array of tubes, wherein the array of magnets and the array of tubes are two-dimensional and each tube of the array of tubes has a different corresponding magnet of the array of magnets; and
providing a raised frame extending around a periphery of the array of magnets such that the raised frame is configured to support the tube holder plate such that the array of tubes is suspended above the array of magnets.

10. The method of claim 9, wherein the array of tubes is suspended above the array of magnets at a height such that each tube of the array of tubes does not come in contact with the corresponding magnet of the array of magnets.

11. The method of claim 9, wherein the array of magnets comprises an array of ring magnets, and wherein the array of tubes is suspended above the array of ring magnets such that the bottom ends of the tubes are not resting within the hollow spaces of the ring magnets at different depths.

12. The method of claim 11, wherein the array of tubes is suspended above the array of ring magnets such that the tube holder plate is leveled with respect to the array of ring magnets.

13. The method of claim 9, wherein the array of magnets is held by a magnet holder plate, and wherein the raised frame comprises a plurality of feet, wherein each foot of the plurality of feet fits into a corresponding hole on the magnet holder plate such that the raised frame is mounted on the magnet holder plate.

14. The method of claim 13, wherein the raised frame is mounted on the magnet holder plate such that the raised frame is raised above the magnet holder plate.

15. The method of claim 9, wherein the raised frame comprises a plurality of collars, wherein each of the collars constrains a x location and a y location of the tube holder plate.

16. The method of claim 15, wherein each of the collars constrains the x location and the y location of the tube holder plate by having a tube of the array of tubes inserted into the collar.

* * * * *